United States Patent [19]

Flynn et al.

[11] Patent Number: 5,643,917
[45] Date of Patent: Jul. 1, 1997

[54] 4-AMINOMETHYL-1-AZAADAMANTANE DERIVED BENZAMIDES

[75] Inventors: Daniel Lee Flynn, Mundelein; Robert L. Shone, Palatine, both of Ill.

[73] Assignee: G. D. Searle & Co., Chicago, Ill.

[21] Appl. No.: 443,545

[22] Filed: May 18, 1995

Related U.S. Application Data

[62] Division of Ser. No. 919,679, Jul. 27, 1992.

[51] Int. Cl.$^6$ ..................... A61K 31/435; C07D 471/18
[52] U.S. Cl. ................. 514/290; 514/294; 546/94; 546/101
[58] Field of Search ................... 514/290, 294; 546/101, 94

[56] References Cited

U.S. PATENT DOCUMENTS

| | | | |
|---|---|---|---|
| 4,578,382 | 3/1986 | Jarreau et al. | 514/245 |
| 4,816,453 | 3/1989 | Watts | 514/217 |
| 4,853,376 | 8/1989 | King | 546/133 X |
| 4,910,193 | 3/1990 | Buchheit | 514/296 X |
| 4,950,759 | 8/1990 | Wijngaarden et al. | 546/94 |
| 4,992,461 | 2/1991 | Zabrowski et al. | 514/413 |
| 5,001,133 | 3/1991 | Richardson et al. | 514/304 |
| 5,140,023 | 8/1992 | Becker et al. | 514/214 |

FOREIGN PATENT DOCUMENTS

| | | |
|---|---|---|
| 85810595 | 12/1985 | European Pat. Off. |
| 8432184 | 12/1984 | United Kingdom . |
| 8717768 | 7/1987 | United Kingdom . |
| 9008069 | 7/1987 | United Kingdom . |

OTHER PUBLICATIONS

CA Sandoz AG New N–oxide(s) of alkylene bridged Piperidinol etc., Derwent Abstract 89/179167/25 B0025, 26 Jun. 1989.

CA: 270144g 1–Azaadamantane derivatives of 5–HT agonists or antagonists. Flynn et al., p. 1044.

*Primary Examiner*—Joseph McKane
*Attorney, Agent, or Firm*—Cynthia S. Kovacevic; Roger A. Williams

[57] ABSTRACT

This invention relates to compounds of the formula:

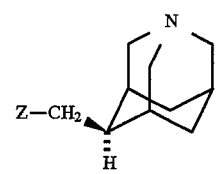

or a pharmaceutically acceptable salt thereof wherein Z is selected from the group consisting of

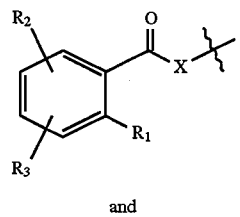

and

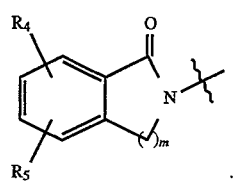

32 Claims, No Drawings

4-AMINOMETHYL-1-AZAADAMANTANE DERIVED BENZAMIDES

This application is a divisional of application Ser. No. 07/919,679 filed Jul. 27, 1992 still pending.

BACKGROUND OF THE INVENTION

The present invention relates to pharmaceutical agents (compounds) which act as $5\text{-HT}_4$ agonists or antagonists and/or $5\text{-HT}_3$ antagonists in mammals. As $5\text{-HT}_4$ agonists, these compounds are gastrointestinal prokinetic agents useful for the treatment of human gastrointestinal (GI) hypomotility disorders such as reflux esophagitis, gastroparesis, nonulcer dyspepsia, ileus, constipation and irritable bowel syndrome (constipation predominant). As $5\text{-HT}_4$ antagonists these compounds are useful in the treatment of motility disorders of the GI tract such as diarrhea and irritable bowel syndrome (diarrhea predominant). As $5\text{-HT}_3$ antagonists these compounds are useful in slowing colonic transport and therefore are useful in the treatment of diarrhea predominant irritable bowel syndrome. The $5\text{-HT}_4$ agonists or antagonists and/or $5\text{-HT}_3$ antagonists are also useful in the treatment of emesis, anxiety, visceral pain, substance abuse (either cravings or withdrawal syndrome), cognitive disorders and other CNS disorders wherein treatment with a serotonin $5\text{-HT}_4$ agonists or antagonists and/or $5\text{-HT}_3$ antagonists would be indicated.

Serotonin (5-hydroxytryptamine; 5-HT) functions as a neurotransmitter in the mammalian central nervous system (CNS) and in the periphery. Serotonin is unsurpassed among monoamine neurotransmitters in the number of receptor subtypes identified. To date, the number of subtypes is into the teens, including the major subtypes 5-HT1A, 1B, 1C, 1D, 1E, 2A, 2B, 3 (perhaps subtypes), 1P, serotonin transporter, etc. Because of the multiplicity of serotonin receptor subtypes, the identification of which serotonin receptor subtype is correlated to various physiological/pharmacological actions is complicated.

Serotonin has been known for some years to promote peristalsis in the GI tract in various animal models. During the mid 1980s, several specific antagonists to the $5\text{-HT}_3$ receptor subtype were identified from independent laboratories. These $5\text{-HT}_3$ antagonists were shown to be prokinetic in various rodent models. Hence, many publications and patents have issued wherein $5\text{-HT}_3$ antagonists are claimed to be useful as GI prokinetic agents to treat various human hypomotility states: reflux esophagitis, nonulcer dyspepsia, gastroparesis, ileus, irritable bowel syndrome.

Gunning and Naylor (J. Pharm. Pharmacol. 1985, 37, 78) reported that metoclopramide (a $5\text{-HT}_3$ antagonist which blocks the $5\text{-HT}_3$-mediated Bezold Jarisch reflex) enhanced electrical-field stimulated contractions in guinea pig stomach strips. Simultaneously, Buchheit et al (J. Pharm. Pharmacol. 1985, 37, 664) reported that three $5\text{-HT}_3$ antagonists [metoclopramide, ICS-205930, and MDL 72222] both enhanced guinea pig stomach muscle strip contraction in vitro and led to increases in gastric emptying rates in vivo. H. Kimura et al (*Jpn. J. Pharmacol.*, 49 (suppl.) Mar. 25–28, 1989, 196pp) independently reported that SN-307, a selective $5\text{-HT}_3$ antagonist, enhanced transit of a charcoal meal in mice. J. S. Gidda et al (Gastroenterology 1988, 95, A867) reported that several $5\text{-HT}_3$ antagonists [ICS-205930, GR38032, and zacopride] enhanced gastric emptying. From these reports it was logically concluded that serotonin $5\text{-HT}_3$ antagonists would be useful agents for the therapeutic treatment of human GI dysmotilities where restoration of peristalsis and enhancement of transit is indicated.

More recently several clinical reports indicate that $5\text{-HT}_3$ antagonists do not accelerate GI transit in man. Talley et al (Digestive Diseases and Sciences 1989, 34, 1511) has reported that GR38032, a selective $5\text{-HT}_3$ antagonist, did not alter small intestinal transit times or mouth-to-cecum transit times. The conclusion was that GR38032 does not have a major effect on GI transit in man. Another clinical report by S. Gore et al (Aliment. Pharmacol. Therap. 1990, 4, 139) has demonstrated that GR38032 not only failed to accelerate GI transit, but in fact slowed colonic transit in man. Thus while $5\text{-HT}_3$ antagonists do accelerate GI transit in rodent species (guinea pig, mouse, rat), they do not affect small bowel transit in man, and decrease, rather than increase, colonic transit.

Canine models of GI transit may more accurately reflect human results. J. M. Van Nueten et al (British J. Pharmacology, 1989, 96, 331P) reported recently that cisapride (a reported $5\text{-HT}_3$ antagonist) enhanced antroduodenal motility in dogs, whereas ICS-205930, another potent $5\text{-HT}_3$ antagonist did not. Moreover, ICS-205930 did not affect the responses to cisapride when the agents were coadministered. Nemeth and Gullikson (European J. Pharmacology, 1989, 166, 387) reported that the ability of BRL-24924 and cisapride to depolarize myenteric neurons was unrelated to their properties of $5\text{-HT}_3$ antagonism.

The receptor mechanism by which cisapride, BRL-24924, metoclopramide, and other serotonergic agents are prokinetic is not related to their $5\text{-HT}_3$ antagonist properties. The receptor mechanism responsible for their prokinetic activities is serotonergic, but at a serotonin receptor subtype, presently referred to as $5\text{-HT}_4$. (M. Tonini et al Pharmacological Research, 1991, 24, 5).

Initially this clarification came from the laboratory of A. Dumuis, M. Sebben and J. Bockaert (Naunyn-Schmiedeberg's Arch. Pharmacol 1989, 340, 403). The prokinetic activity of a variety of benzamides, including cisapride and BRL-24924, were found to correlate with agonist activity at a novel $5\text{-HT}_4$ receptor subtype identified in mouse embryonic colliculi neurons. Shortly thereafter, D. Craig and D. Clarke identified the $5\text{-HT}_4$ receptor in the myenteric plexus of the guinea pig ileum (J. Pharmacol. Exp. Ther., 1990, 252, 1378). Quite recently Craig and Clarke also demonstrated that the peristaltic reflex evoked by serotonin and the benzamide BRL-24924 (renzapride) was mediated through agonism at $5\text{-HT}_4$ receptors. The compounds of the present invention exhibit potent activity in a $5\text{-HT}_4$ agonism in vitro functional assay compared to its epimer and previously disclosed compounds.

E. A. Watts (U.S. Pat. No. 4,816,453 1989) discloses N-heterocyclic derivatives of benzamides useful in treating gastric and intestinal disorders and as $5\text{-HT}_3$ antagonists including the following compounds hereinafter referred to as B-#1 and B-#2:

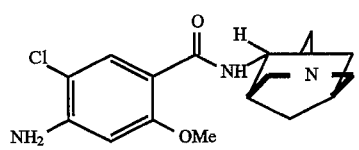

-continued

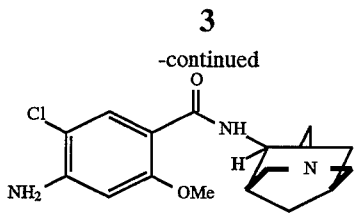
B-#2

As is shown in the 5-HT$_4$ agonism assays described herein, the compounds of the present invention show superior 5-HT$_4$ agonist activity over B-#1 and B-#2.

There is a need in the area of serotonin regulation for agents with broad clinical usefulness. Serotonin is one of the newer neurotransmitters to be recognized for physiological importance and agents which interact with 5-HT receptors are currently the focus of much research. P. Bonate, *Clinical Neuropharmacology*, Vol. 14, No. 1, pp. 1–16 (1991).

Accordingly, it is the object of this invention to produce compounds for use as pharmaceutical agents which will exhibit 5-HT$_4$ agonist or antagonist and/or 5-HT$_3$ antagonist activity in mammals. The compounds of the present invention meet the need for an agent which has broad clinical usefulness for treating conditions affected by 5-HT$_4$ agonists or antagonists and/or 5-HT$_3$ antagonists in mammals by administering therapeutically effective amount of the compounds.

SUMMARY OF THE INVENTION

This invention relates to compounds of the formula I

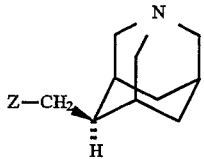
(I)

or a pharmaceutically acceptable salt thereof wherein Z is selected from the group consisting of

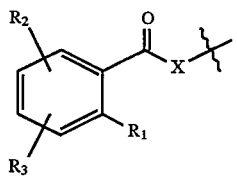

and

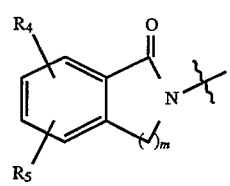

R$_1$ is alkoxy of one to six carbon atoms;

R$_2$, R$_3$, R$_4$ and R$_5$ are the same or different and are selected from the group consisting of hydrogen, halogen, CF$_3$, hydroxy, alkoxy of one to six carbon atoms, acyl of two to seven carbon atoms, amino, amino substituted by one or two alkyl groups of one to six carbon atoms, C$_2$–C$_7$ acylamino, aminocarbonyl, aminosulfone optionally substituted by one or two alkyl groups of one to six carbon atoms, C$_1$–C$_6$ alkylsulfone and nitro;

m is 1 or 2;

X is 0 or NR$_7$; and

R$_7$ is hydrogen or alkyl of one to six carbon atoms.

The present invention also provides pharmaceutical compositions comprised of a therapeutically effective amount of the compounds of Formula I in combination with a pharmaceutically acceptable carrier and a method for treating conditions responsive to 5-HT$_4$ agonist or antagonist and/or 5-HT$_3$ antagonist compositions.

DETAILED DESCRIPTION OF THE INVENTION

This invention encompasses compounds of the Formula I as previously described.

Within the class of compounds defined by Formula I, there is a sub-class of preferred compounds represented by Formula II:

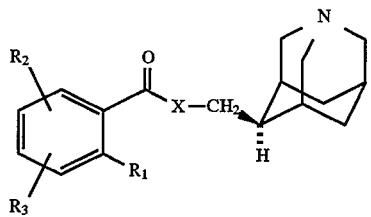

or a pharmaceutically acceptable salt thereof

R$_1$ is alkoxy of one to six carbon atoms;

R$_2$, R$_3$, R$_4$ and R$_5$ are the same or different and are selected from the group consisting of hydrogen, halogen, CF$_3$, hydroxy, alkoxy of one to six carbon atoms, acyl of two to seven carbon atoms, amino, amino substituted by one or two alkyl groups of one to six carbon atoms, C$_2$–C$_7$ acylamino, aminocarbonyl, aminosulfone optionally substituted by one or two alkyl groups of one to six carbon atoms, C$_1$–C$_6$ alkylsulfone and nitro;

m is 1 or 2;

X is NR$_7$; and

R$_7$ is hydrogen or alkyl of one to six carbon atoms.

Included within the preferred subclass of compounds of the Formula II is:

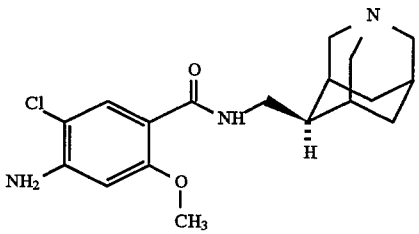

exo-4-amino-N-(1-azacyclo[3.3.1.1$^{3,7}$]decan-4-ylmethyl)-5-chloro-2-methoxy benzamide.

Included within the classes and subclasses of compounds embraced by Formulas I–II are pharmaceutically acceptable salts of such compounds.

In the structures herein a bond drawn across a bond in a ring indicates that the bond can be to any available atom of the ring structure.

The term "pharmaceutically acceptable salt," as used herein, refers to conventionally accepted pharmaceutical salts prepared by processes which are well known to those of ordinary skill in the art. [See for example, S. M. Berge, et al., "Pharmaceutical Salts," *J. Pharm. Sci.*, 66:1–19 (1977)].

The term "composition" as used herein means a product which results from the mixing or combining of more than one element or ingredient.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a chemical agent from one organ or portion of the body to another organ or portion of the body.

The term "therapeutically effective amount" shall mean that amount of drug or pharmaceutical agent that will elicit the biological or medical response of a tissue, system or animal that is being sought by a researcher or clinician.

The term "alkyl" as used herein means a univalent hydrocarbon radical having from one to twelve carbon atoms, more preferably from one to six carbon atoms and derived by the removal of a single hydrogen atom from a straight or branched chain saturated hydrocarbon. Representative of such radicals are methyl, ethyl, n-propyl, isopropyl, n-butyl, sec-butyl, isobutyl, tert-butyl, n-octyl, 2,4-dimethylpentyl and the like.

The term "alkoxy" as used herein means an alkyl radical, as defined above having one or more oxygen atoms attached thereto. Representative alkoxy groups include methoxy, ethoxy, propoxy, tert-butoxy and the like.

The term "halogen" as used herein means a fluoro, chloro, bromo or iodo radical.

The term "amino" as used herein is represented by the radical —$NR_8R_9$ wherein $R_8$ and $R_9$ are independently hydrogen or an alkyl group as previously described.

The term "acylamino" as used herein is represented by the radical

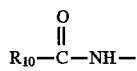

wherein $R_{10}$ is an alkyl group as described above.

The term "aminosulfone" as used herein is represented by the radical $R_4$—$SO_2$—NH— wherein $R_4$ is an alkyl group as defined above.

The term "aminocarbonyl" as used herein is represented by the radical

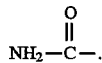

The compounds herein exhibit 5-$HT_4$ agonism or antagonism and/or 5-$HT_3$ antagonism. The 5-$HT_3$ activity possessed by the compounds of this invention was determined by the radioligand receptor binding assay as described herein. 5-$HT_4$ agonist activity was determined in the in vitro rat tunica muscularis mucosae (TMM) assay described herein. (Baxter et al., Naunyn Schmied Arch. Pharmacol, 1991, 343,439). One with skill in the art could determine the activity of the compounds of the present invention using the methodology of these assays, described herein, without undue experimentation.

By virtue of their activity as 5-$HT_4$ agonists or antagonists and/or 5-$HT_3$ antagonists the compounds of Formula I and II are useful in treating conditions such as gastrointestinal motility disorders, emesis, anxiety, cognitive disorders and other CNS disorders. As used herein gastrointestinal motility disorders responsive to treatment with 5-$HT_4$ agonists include reflux esophagitis, non-ulcer dyspepsia, gastroparesis, ileus, irritable bowel syndrome (constipation predominant), constipation, and the like. As used herein gastrointestinal motility disorders responsive to treatment with 5-$HT_4$ antagonists include diarrhea, irritable bowel syndrome (diarrhea predominant) and the like. As used herein disorders responsive to 5-$HT_3$ antagonists include emesis due to either cancer chemotherapy or post-operative, anxiety, cognitive disorders, drug abuse (either cravings or withdrawal syndrome), irritable bowel syndrome (diarrhea predominant) and the like. A physician or veterinarian of ordinary skill can readily determine whether a subject exhibits such a condition treatable with a 5-$HT_3$ antagonist or 5-$HT_4$ agonist.

The compounds of the present invention can be administered in such oral dosage forms as tablets, capsules, softgels, pills, powders, granules, elixirs or syrups. The compounds can also be administered intravascularly, intraperitoneally, subcutaneously, intramuscularly or topically using forms known to the pharmaceutical art. In general the preferred form of administration is oral.

For the orally administered pharmaceutical compositions and methods of the present invention, the foregoing active ingredients will typically be administered in admixture with suitable pharmaceutical diluents, excipients or carriers (collectively referred to hereinafter as "carrier" materials). Such carrier materials are suitably selected with respect to the intended form of administration and consistent with conventional pharmaceutical practices.

For example, for oral administration in the form of tablets or capsules, a therapeutically effective amount of one or more compounds of the present invention can be combined with any oral pharmaceutically acceptable inert carrier such as lactose, starch, sucrose, cellulose, magnesium stearate, calcium sulfate and the like or various combinations thereof. For oral administration in liquid forms, such as in softgels, elixirs, syrups and the like, a therapeutically effective amount of the active drug components can be combined with any oral pharmaceutically acceptable inert carrier such as water, ethanol, polyethylene glycol, vegetable oils, propylene glycol, benzylalcohol and the like or various combinations thereof.

When desired or necessary, suitable binders, lubricants, disintegrating agents, preservatives, and coloring or flavoring agents can also be incorporated into the mixture. Suitable binders include starch, gelatin, natural sugars, corn sweeteners, natural and synthetic gums and waxes and the like, or combinations thereof. Lubricants can include boric acid, sodium benzoate, sodium acetate, sodium chloride and the like, or combinations thereof. Disintegrators include without limitation starch, methylcellulose, agar, bentonite, guar gum and the like, or combinations thereof.

For intravascular, intraperitoneal, subcutaneous or intramuscular administration, one or more compounds of the present invention can be combined with a suitable carrier such as water, saline, aqueous dextrose and the like. For topical administration therapeutically effective amounts of one or more compounds of the present invention can be combined with pharmaceutically acceptable creams, oils, waxes, gels and the like.

Regardless of the route of administration selected, a therapeutically effective amount of the compounds of the present invention are formulated into pharmaceutically acceptable dosage forms by conventional methods known to those skilled in the art. The dosages for preventing or treating conditions mediated by 5-$HT_4$ agonists or antagonists and/or 5-$HT_3$ antagonists with the compounds of the present invention is determined in accordance with a variety of factors, including the type, age, weight, sex and medical condition of patient, the severity of the condition, the route of administration and the particular compound employed in the treatment. A physician or veterinarian of ordinary skill can readily determine and prescribe the effective amount of drug required to prevent or arrest progress of the condition. In so proceeding, the physician or veterinarian could employ relatively low doses at first and subsequently increase the dose until a maximum response is obtained. The daily doses of the compounds of the invention are ordinarily in the range of about 1 to 1000 mg, more preferably in the range of about 10 to 500 mg.

The compounds of this invention are generally prepared according to the following reaction schemes I–II.

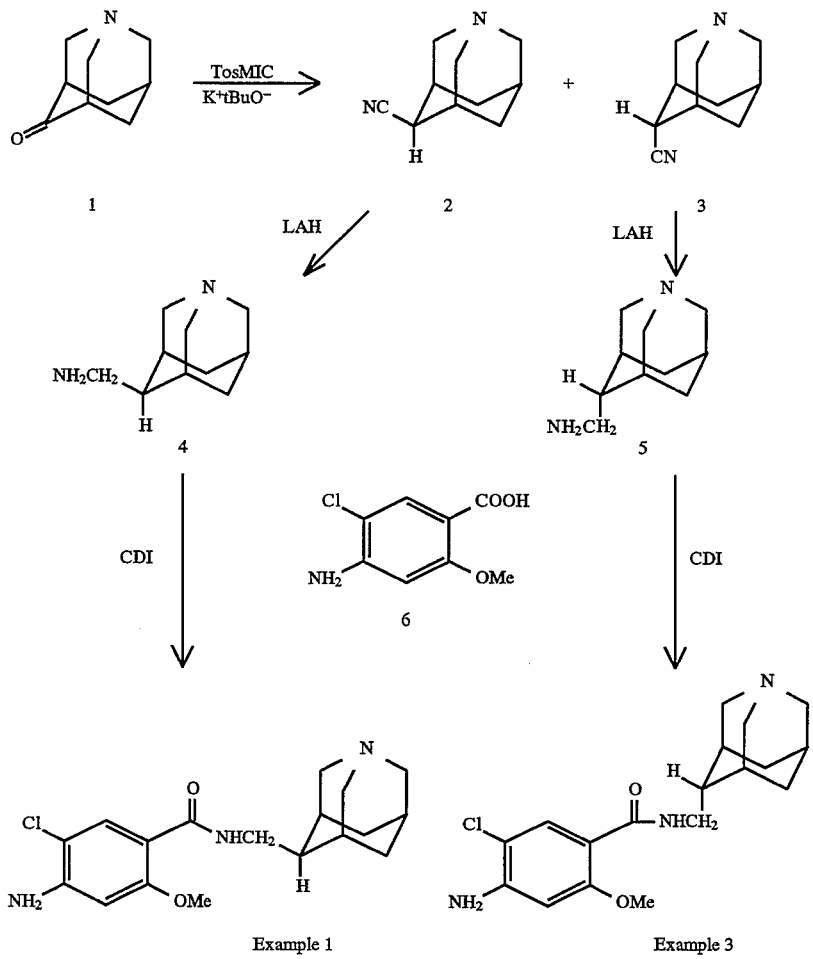

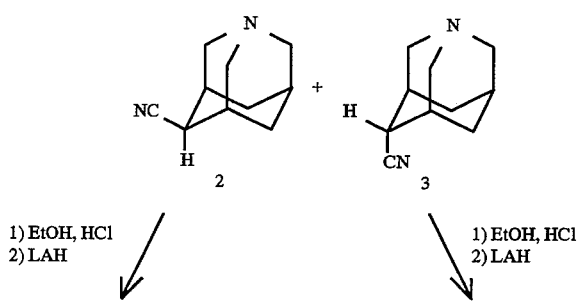

-continued
SCHEME II

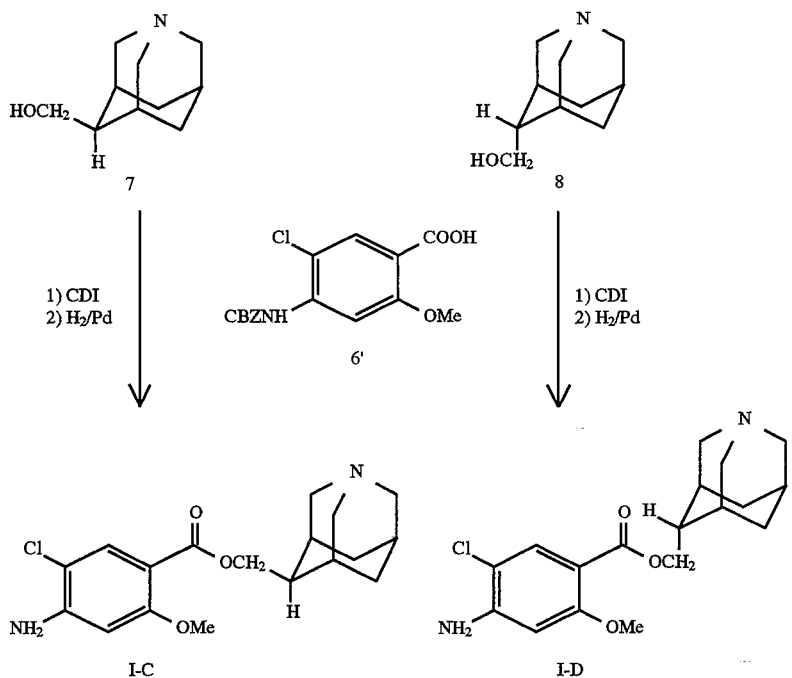

In Scheme I, the known compound 1-azaadamantane-4-one 1 (R. M. Black, *Synthesis* 1981, 829) is reacted with tosylmethylisocyanide (TosMiC) in the presence of potassium t-butoxide to afford the exo- and endo-1-azaadamantane-4-nitriles 2 and 3, which are separated by silica gel chromatography (4% MeOH (NH$_3$)/chloroform). These nitriles are separately reduced with lithium aluminum hydride (LAH) in tetrahydrofuran (room temperature to reflux) to give the exo- and endo-1-azaadamantane-4-methylamines 4 and 5, respectively. These amines are then condensed with 5-chloro-4-amino-2-methoxybenzoic acid 6 in the presence of the coupling agent carbonyldiimidazole (CDI) in tetrahydrofuran or dimethylformamide to afford the desired benzamides of Examples 1 and 3.

In Scheme II, the nitriles 2 and 3 are treated with ethanolic HCl to afford the corresponding esters, which are then reduced with lithium aluminum hydride (LAH) in tetrahydrofuran to give the alcohols 7 and 8. Coupling of these alcohols with the substituted benzoic acid 6' using, by way of example, carbonyldiimidazole (CDI) in tetrahydrofuran or dimethylformamide, followed by removal of the carbobenzyloxy protecting group, affords the desired ester compounds I-C and I-D.

The following examples illustrate the methods used to prepare the compounds of this invention. These examples are given by way of illustration only and are not meant to be construed as limiting the invention in spirit or scope, as many modification in materials and methods will be apparent from this disclosure to one having ordinary skill in the art.

EXAMPLE A

Exo and Endo 4-cyano-1-azaadamantanes

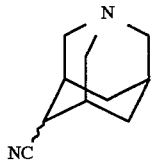

A solution of 923 mg (6.1 mmol) of 1-azaadamantane-4-one and 1.542 g (7.9 mmol) of tosylmethyl isocyanide in 21 ml of dry dimethoxyethane and 0.62 ml of absolute ethanol was cooled to −10° C. (ice-methanol). Potassium t-butoxide, 1.63 g (14.5 mmol), was added as a solid in five portions over 15 minutes. The reaction mixture was warmed to room temperature, stirred for two hours and was warmed to 40° C. for 15 min. The reaction mixture was filtered to remove precipitated solids and the filtrate was concentrated to provide an oil. The oil was dissolved in 7 ml of water, saturated with NaCl and extracted five times with 15 ml portions of ether. The ether extracts were dried over magnesium sulfate (MgSO$_4$), filtered and the ether evaporated to give 1.01 g of crude nitrile. Purification by low pressure chromatography on silica gel (4% MeOH/NH$_3$—CHCl$_3$) gave 0.38 g (38%) of the nonpolar isomer, exo-4-cyano-1-azaadamantane and 0.41 g (41%) of the polar isomer, endo-4-cyano-1-azaadamantane.

EXAMPLE B

Endo-4-aminomethyl-1-azaadamantane

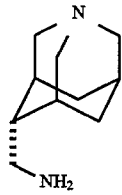

A solution of 3.8 ml of 1.0M lithium aluminum hydride (3.80 mmol) in THF was cooled in an ice/methanol bath. Next 0.41 g (2.53 mmol) of endo 4-cyano-1-azaadamantane in 6 ml of THF was added and the mixture was allowed to warm to room temperature and then refluxed for two hours. After cooling the aluminum salts were precipitated by adding 144 µl of water in 2 ml of THF, 144 µl of 15% sodium hydroxide solution and 433 µl of water. The granulated aluminum salts were removed by filtration and the filtrate was concentrated to provide 382 mg (91%) of crude amine as a light yellow oil. $^1$H NMR δ2.83 (d, 2H) and 2.88 (d, 2H), exocyclic aminomethyl $CH_2$, in a 85/15 ratio that corresponds to a endo/exo mixture of 4-aminomethyl-1-azaadamantanes.

EXAMPLE C

Exo 4-aminomethyl-1-azaadamantane

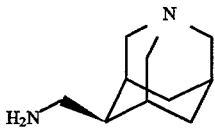

A solution of 0.38 g (2.34 mmol) of exo 4-cyano-1-azaadamantane in 8 ml of THF was added rapidly to a stirred solution of 4 ml of 1.0M lithium aluminum hydride (4 mmol) in THF at room temperature. The resulting mixture was refluxed for 2 hours, cooled overnight and quenched by addition of 0.152 ml of water, 0.152 ml of 15% sodium hydroxide solution and 0.456 ml of water. The granulated aluminum salts were removed by filtration and the THF was evaporated to give 351 mg (90%) of the amine as an oil. $^1$H NMR δ2.88 (d, 2H), 4-aminomethyl $CH_2$. $^{13}$C NMR δ26.3 (C-7), 28.2 (C-3,5), 36.9 (C-6,10), 42.8 (C-11), 46.2 (C-4), 52.0 (C-2,9), 58.3 (C-8).

EXAMPLE 1

Endo-4-amino-N-(1-azacyclo[3.3.1.1$^{3,7}$]decan-4-ylmethyl)-5-chloro-2-methoxybenzamide

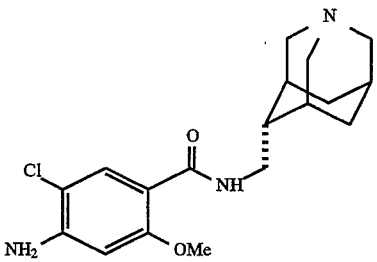

A solution of 464 mg (2.3 mmol) of 2-methoxy-4-amino-5-chlorobenzoic acid in 2.9 ml of dimethylformamide was treated with 373 mg (2.3 mmol) of carbonyldiimidazole and stirred for one hour. A solution of 382 mg (2.3 mmol) of the 85/15 endo/exo mixture of 4-aminomethyl-1-azaadamantane in 0.5 ml of dimethylformamide was added and the mixture was stirred overnight. The DMF was removed by evaporation at reduced pressure, the residue was dissolved in 100 ml of chloroform and was washed with 25 ml of dilute $NaHCO_3$ solution, 25 ml of brine and dried ($MgSO_4$). Evaporation of the $CHCl_3$ gave 879 mg of a crude yellow oil that was purified on silica gel by elution with 15% methanol ($NH_3$)/chloroform to give 310 mg (39%) of the endo benzamide as a glass that is a 0.25 $CHCl_3$ solvate. $^1$H NMR δ1.63 (m, 8 H), 2.07–2.20 (m, 3 H), 3.05–3.30 (m, 6 H), 3.62 (dd, 2 H), 3.90 (s, 3 H), 4.42 (bs, 2 H), 6.30 (s, 1 H), 7.67 (bt, 1 H), 8.12 (s, 1 H). HPLC: 96.9% endo amide, 1.6% exo amide and 1.5% impurity.

EXAMPLE 2

Endo-4-amino-N-(1-azacyclo[3.3.1.1$^{3,7}$]decan-4-ylmethyl)-5-chloro-2-methoxybenzamide hydrochloride

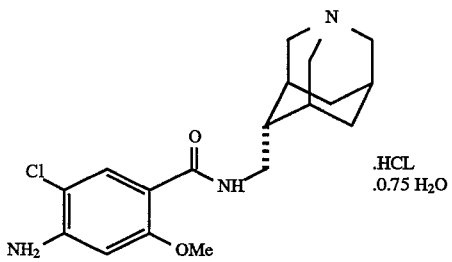

A solution of 225 mg (0.593 mmol) of the endo benzamide in 7 ml of methanol was cooled in an ice/methanol bath and treated with 46.6 mg (0.593 mmol) or 42.1 µl of acetyl chloride. After warming to room temperature the methanol was removed in a stream of nitrogen and the residue was stirred vigorously with 15 ml of ether. Evaporation of the ether gave 218 mg (92%) of the benzamide hydrochloride hydrate as a yellow powder. Anal. Calcd. for $C_{18}H_{24}N_3O_2Cl/HCl/0.75\ H_2O$ (399.84); C, 54.07; H, 6.68; N, 10.51; Cl, 17.73. Found: C, 54.02; H, 6.45; N, 10.38; Cl, 17.87. $^1$H NMR ($CD_3OD$), 1.84–2.37 (m, 8 H), 3.45–3.68 (m, 8 H), 3.91 (s, 3 H), 6.52 (s, 1 H), 7.79 (s, 1 H).

EXAMPLE 3

Exo-4-amino-N-(1-azacyclo[3.3.1.1$^{3,7}$]decan-4-ylmethyl)-5-chloro-2-methoxybenzamide

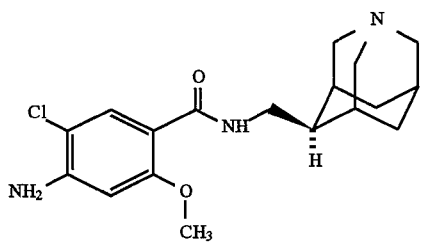

Carbonyldiimidazole, 350 mg (2.16 mmol), was added to a solution of 436 mg (2.16 mmol) of 2-methoxy-4-amino-5-chlorobenzoic acid in 2.7 ml of dimethylformamide (DMF) and the mixture was stirred for 1 hour. A solution of 351 mg (2.16 mmol) of exo-4-aminomethyl-1-azaadamantane in 0.5 ml of DMF was added and the mixture was stirred overnight. The DMF was evaporated at reduced pressure, the residue dissolved in 100 ml chloroform and the chloroform was washed with 25 ml of dilute NaHCO$_3$, 25 ml of brine and dried (MgSO$_4$). Evaporation of the chloroform gave 837 mg of crude waxy solid that was purified on silica gel by elution with 20% methanol (NH$_3$)/chloroform to give 470 mg (62%) of white solid. Anal. Calcd. for C$_{18}$H$_{24}$N$_3$O$_2$Cl (349.86); C, 61.80; H, 6.91; N, 12.01; Cl, 10.13. Found: C, 61.60; H, 6.86; N, 11.80; Cl, 10.79. m/e=349. $^1$H NMR δ 1.59 (bs, 2 H), 1.71 (bs, 1 H), 1.88–2.18 (m, 5 H), 2.97 (d, 2 H), 3.13 (s, 2 H), 3.37 (d, 2 H), 3.65 (dd, 2 H), 3.89 (s, 3 H), 4.38 (bs, 2 H), 6.30 (s, 1 H)7 7.69 (bt, 1 H), 8.13 (s, 1 H). HPLC: 99.2% exo benzamide, 0.8% endo benzamide.

EXAMPLE 4

Exo-4-amino-N-(1-azacyclo[3.3.1.1$^{3,7}$]decan-4-ylmethyl)-5-chloro-2-methoxybenzamide, hydrochloride

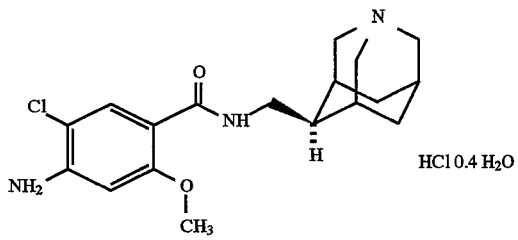

A solution of 333 mg (0.953 mmol) of the exo benzamide in 5 ml of methanol was cooled in an ice/methanol bath and 74.8 mg (0.953 mmol) or 67.8 µl of acetyl chloride was added dropwise. After addition the mixture was warmed to room temperature and the methanol was evaporated in a stream of nitrogen. The residual solid was stirred rapidly with 15 ml of ether for one hour and the ether was removed by evaporation to give 368 mg (93%) of hydrochloride as a vanilla powder. Anal. Calcd. for C$_{18}$H$_{24}$N$_3$O$_2$Cl/HCl/0.4 H$_2$O (393.53); C, 54.94; H, 6.61; N, 10.68; Cl, 18.02. Found: C, 54.93; H, 6.51; N, 10.50; Cl, 18.31. HPLC: 99.1% exo benzamide hydrochloride, 0.9% impurity.

EXAMPLE 5

Preparation of phthalimidines

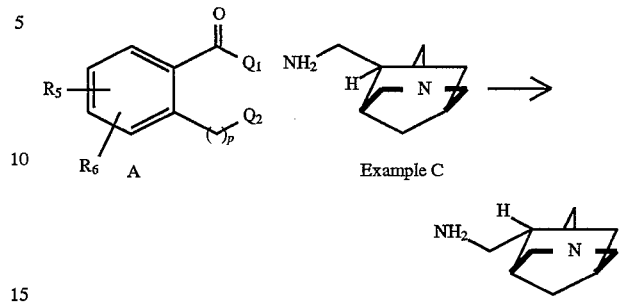

Example C

Example B

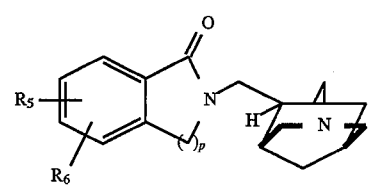

EXAMPLE 5A

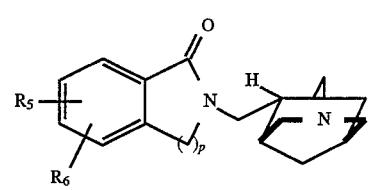

EXAMPLE 5B

A compound of general formula A, wherein Q$_1$ and Q$_2$ are independently leaving groups (eg. chloride) or taken together are oxygen, p is 1 or 2, and R$_5$ and R$_6$ are as defined above, is reacted with the amines of examples B and C in an inert solvent such as toluene, tetrahydrofuran, or dimethylformamide optionally in the presence of a base such as potassium carbonate or cesium carbonate to afford the desired phthalimidines.

A. In Vitro Functional Assay for Serotonin 5-HT$_4$ agonism: RAT TMM

Serotonin 5-HT$_4$ agonism was measured in the rat esophagus in vitro preparation as reported by Baxter et al (Naunyn. Schmied. Arch. Pharmacol. 1991, 343, 439). Agonist activity was determined utilizing relaxation of carbachol-contracted rat tunica muscularis mucosae. One 2 cm segment of intrathoracic esophagus proximal to the diaphragm was removed from male rats, weighing approximately 300 gm, and the outer muscle layers removed. The inner tunica muscularis mucosa was mounted under 0.2–0.3 g of tension in a tissue bath containing oxygenated Tyrode's solution at 37° C. Cortisterone acetate (30 µM) and fluoxetine (1 µM) were included in the buffer to prevent uptake of serotonin, as well as pargyline (10 µM) to inhibit monoamine oxidase. Following a 30 min equilibrium period, tissues were isometrically contracted with carbachol (3 µM) to obtain a tonic contraction. A stable plateau was obtained within 20 min when test compound was added cumulatively to relax the muscle strip. EC$_{50}$ values were obtained for each agonist in tissues from 5 rats. EC$_{50}$ values for agonists at this 5-HT$_4$ receptor are indicated in Table I.

B. Canine Gastric Emptying In Vivo Model

Determination of the effects of test compounds on gastric emptying of solid meals in nonsedated dogs was done in separate experiments in an alpha-2 adrenergic model of gastroparesis as described in Gullickson et al., *J. Pharmacol.*

Exp. Ther., 258: 103–110 (1991) and Gullikson et al., Gastrointest. Liver Physiol., 261 (1991).

Dogs weighing 15–25 kg were trained to stand quietly in Pavlov slings for 3–4 hours and consistent control emptying responses were obtained prior to use in gastric emptying experiments with the test compounds.

The solid meal consisted of 2 cooked scrambled eggs which were divided into 1 cm sized pieces and mixed with beef stew. One mCi of Tc-99m sulfur colloid was incorporated into the eggs prior to cooking. The dogs were fasted for at least 24 hours prior to the study and were fed the solid meal by intragastric tube. To delay normal gastric emptying 0.030 mg/kg of an alpha-2 adrenergic agonist of the formula

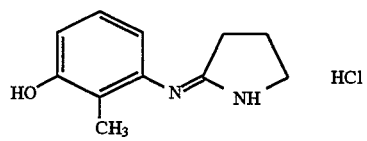

was administered immediately following the meal. The test compounds were given by capsule 45 min. prior to feeding.

A Siemens 370 ZLC gamma camera with high resolution low energy collimator was used to acquire left lateral images during emptying studies. Acquisition times were 3 min/frame for 180 min solid emptying. Disappearance of contents from the stomach region of interest was plotted over time to obtain emptying curves. The amount of solid meal remaining in the stomach at the end of each experiment and the fractional solid emptying rate (% emptied per min) were calculated from linear regression equations describing solid emptying.

Emptying measurements obtained from one replicate of each drug treatment were compared to the means of at least 3 control responses for the alpha-2 adrenergic agonist in solid emptying studies. The results obtained for Example 4 and cisapride are reported in Table I.

TABLE I

| Entry | 5-HT$_4$ Agonism (Rat TMM) In Vitro Assay: EC50 values | Canine Solid Gastric Emptying (% Control to Treat) |
|---|---|---|
| Serotonin | 9 nM | — |
| Example 2 | 545 nM | — |
| Example 4 | 74 nM | 20.2% to 35.1% emptied at 0.3 mg/kg IV |
| B - # 1 | 262 nM | |
| B - # 2 | 538 nM | |
| Cisapride | 55 nM | 23.2% to 36.6% emptied at 0.3 mg/kg IG |

C. Serotonin 5-HT$_3$ Receptor Binding Assay
Preparation of Membrane Suspensions NG108-15 neuroblastoma cells were cultured at 37° C. in closed culture flasks for 3–4 days or to confluence (6-16×10$^6$ cells/flask). The cells were superficially rinsed twice (10 ml) with chilled 20 mM Tris buffer containing 154 mM NaCl (pH=7.4 at 25° C.), and then harvested. The cells were centrifuged at 900×g for five minutes at 4° C. At this point the cells could be frozen. The (frozen or freshly prepared) pellets from each flask were suspended in 4 ml buffer and homogenized a second time as above. The resulting supernatant was used for radioligand binding studies.

Binding Assay

To each well of a microtiter plate were added 100 µl tissue, 50 µl [$^3$H]GR65630 (4 nM stock, SA=64 Ci/mmol from Dupont/NEN) and 50 µl drugs. Nonspecific binding was measured in the presence of 10 µM zacopride. Reactions were incubated for 45–60 minutes at 25° C. followed by filtration under reduced pressure through GF/B-type filters with the aid of either a Brandel or Skatron macro harvester. The filters were washed with ice-cold buffer (a 6 sec wash time on the Skatron harvester, using filters presoaked with polyethylenimine) and specific binding was measured by either a Packard CA 1900 or an LKB Betaplate counter. Under these conditions the Kd is 1.5 nM for [$^3$H]GR65630 with a Bmax of 195 fmole/mg protein. At 1 nM, the ratio of total to nonspecific binding is on the order of 6:1 with a total binding of around 800 CPM. IC$_{50}$ values were determined for test drugs, and Ki values calculated from the equation:

apparent Ki=IC$_{50}$/(1+*L/Kd*), where *L is the concentration of radioligand used (1 nM) and *Kd is the dissociation constant of the radioligand (1.5 nM).

TABLE II

| ENTRY | Ki (5-HT$_3$ receptors) |
|---|---|
| Example 2 | 143.7 nM |
| Example 4 | 25.7 nM |
| B - # 1 | 2.9 nM |
| B - # 2 | 170.7 nM |
| Cisapride | 1500 nM |

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula:

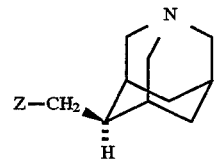

or a pharmaceutically acceptable salt thereof wherein Z is selected from the group consisting of

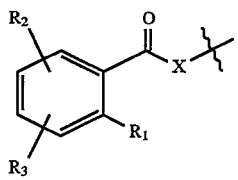

and

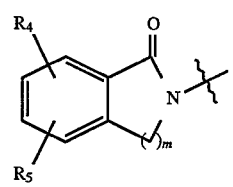

R$_1$ is alkoxy of one to six carbon atoms;

R$_2$, R$_3$, R$_4$ and R$_5$ are the same or different and are selected from the group consisting of hydrogen, halogen, CF$_3$, hydroxy, alkoxy of one to six carbon atoms, acyl of two to seven carbon atoms, amino, amino substituted by one or two alkyl groups of one to six carbon atoms, $C_2$–$C_7$ acylamino, aminocarbonyl, aminosulfone optionally substituted by one or two alkyl groups of one to six carbon atoms, $C_1$–$C_6$ alkylsulfone and nitro;

m is 1 or 2;

X is O or $NR_7$; and $R_7$ is hydrogen or alkyl of 1 to 6 carbon atoms.

2. A compound as recited in claim 1 wherein Z is

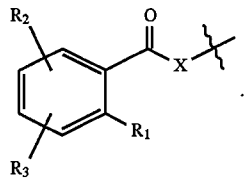

3. A compound as recited in claim 2 wherein X is NH.

4. A compound as recited in claim 3 wherein $R_1$ is methoxy.

5. A compound as recited in claim 4 wherein $R_2$ is amino.

6. A compound as recited in claim 5 wherein $R_3$ is halogen.

7. A compound as recited in claim 3 wherein $R_1$ is methoxy, $R_2$ is amino and $R_3$ is halogen.

8. A compound as recited in claim 7 of the formula

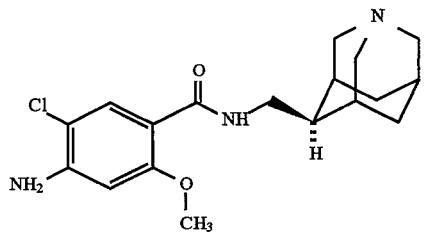

9. A pharmaceutical composition comprising a compound of the formula:

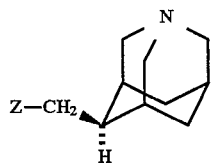

or a pharmaceutically acceptable salt thereof wherein Z is selected form the group consisting of

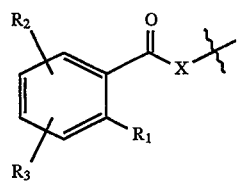

-continued
and

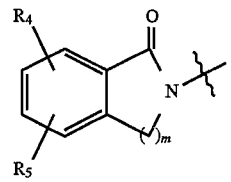

$R_1$ is alkoxy of one to six carbon atoms;

$R_2$, $R_3$, $R_4$ and $R_5$ are the same or different and are selected from the group consisting of hydrogen, halogen, $CF_3$, hydroxy, alkoxy of one to six carbon atoms, acyl of two to seven carbon atoms, amino, amino substituted by one or two alkyl groups of one to six carbon atoms, $C_2$–$C_7$ acylamino, aminocarbonyl, aminosulfone optionally substituted by one or two alkyl groups of one to six carbon atoms, $C_1$–$C_6$ alkylsulfone and nitro;

m is 1 or 2;

X is O or $NR_7$; and $R_7$ is hydrogen or alkyl of 1 to 6 carbon atoms.

10. A pharmaceutical composition as recited in claim 9 wherein Z is

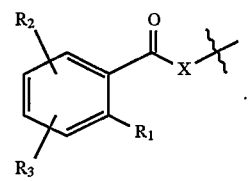

11. A pharmaceutical composition as recited in claim 10 wherein X is NH.

12. A pharmaceutical composition as recited in claim 11 wherein $R_1$ is methoxy.

13. A pharmaceutical composition as recited in claim 12 wherein $R_2$ is amino.

14. A pharmaceutical composition as recited in claim 13 wherein $R_3$ is halogen.

15. A pharmaceutical composition as recited in claim 11 wherein $R_1$ is methoxy, $R_2$ is amino and $R_3$ is halogen.

16. A pharmaceutical composition as recited in claim 15 wherein the compound is of the formula:

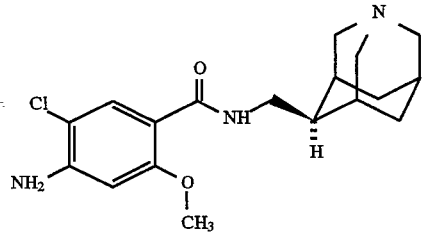

17. A method of treating conditions responsive to 5-$HT_4$ agonists comprising administering to a mammal in need of such treatment a compound of the formula:

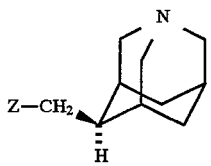

or a pharmaceutically acceptable salt thereof wherein Z is selected from the group consisting of

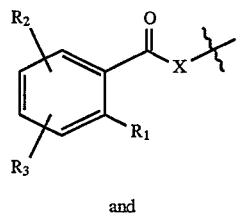

and

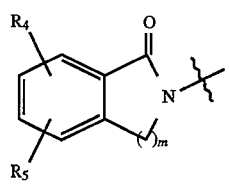

wherein

R$_1$ is alkoxy of one to six carbon atoms;

R$_2$, R$_3$, R$_4$ and R$_5$ are the same or different and are selected from the group consisting of hydrogen, halogen, CF$_3$, hydroxy, alkoxy of one to six carbon atoms, acyl of two to seven carbon atoms, amino, amino substituted by one or two alkyl groups of one to six carbon atoms, C$_2$–C$_7$ acylamino, aminocarbonyl, aminosulfone optionally substituted by one or two alkyl groups of one to six carbon atoms, C$_1$–C$_6$ alkylsulfone and nitro;

m is 1 or 2;

X is O or NR$_7$; and

R$_7$ is hydrogen or alkyl of 1 to 6 carbon atoms.

18. A method as recited in claim 17 wherein Z is

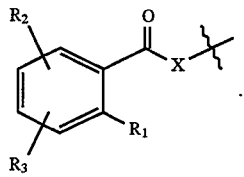

19. A method as recited in claim 18 wherein X is NH.

20. A method as recited in claim 19 wherein R$_1$ is methoxy.

21. A method as recited in claim 20 wherein R$_2$ is amino.

22. A method as recited in claim 21 wherein R$_3$ is halogen.

23. A method as recited in claim 19 wherein R$_1$ is methoxy, R$_2$ is amino and R$_3$ is halogen.

24. A method as recited in claim 23 wherein the compound is of the formula

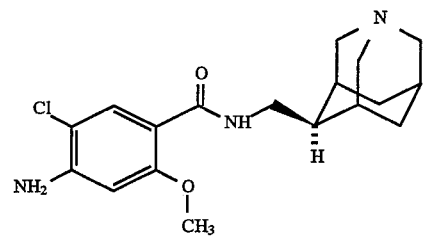

25. A method of treating conditions responsive to 5-HT$_3$ antagonism comprising administering to a mammal in need of such treatment a compound of the formula:

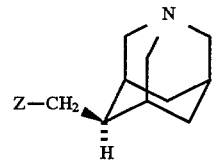

or a pharmaceutically acceptable salt thereof wherein Z is selected from the group consisting of

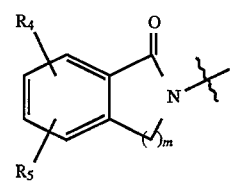

and

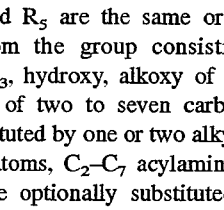

wherein

R$_1$ is alkoxy of one to six carbon atoms;

R$_2$, R$_3$, R$_4$ and R$_5$ are the same or different and are selected from the group consisting of hydrogen, halogen, CF$_3$, hydroxy, alkoxy of one to six carbon atoms, acyl of two to seven carbon atoms, amino, amino substituted by one or two alkyl groups of one to six carbon atoms, C$_2$–C$_7$ acylamino, aminocarbonyl, aminosulfone optionally substituted by one or two alkyl groups of one to six carbon atoms, C$_1$–C$_6$ alkylsulfone and nitro;

m is 1 or 2;

X is O or NR$_7$; and

R$_7$ is hydrogen or alkyl of 1 to 6 carbon atoms.

26. A method as recited in claim 25 wherein Z is

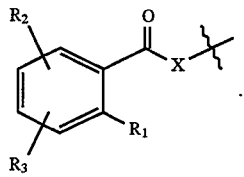

27. A method as recited in claim 26 wherein X is NH.

28. A method as recited in claim 27 wherein $R_1$ is methoxy.
29. A method as recited in claim 28 wherein $R_2$ is amino.
30. A method as recited in claim 29 wherein $R_3$ is halogen.
31. A method as recited in claim 30 wherein $R_1$ is methoxy, $R_2$ is amino and $R_3$ is halogen.
32. A method as recited in claim 31 of wherein the compound is of the formula
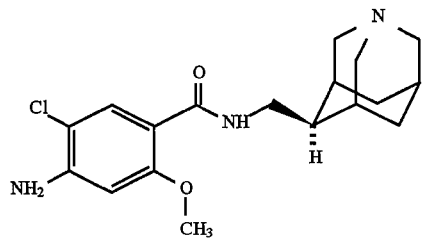
* * * * *